(12) United States Patent
Suyama

(10) Patent No.: US 8,981,310 B2
(45) Date of Patent: Mar. 17, 2015

(54) RADIATION DETECTING DEVICE

(75) Inventor: Toshiyasu Suyama, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 191 days.

(21) Appl. No.: 13/391,030

(22) PCT Filed: Jun. 29, 2010

(86) PCT No.: PCT/JP2010/061018
§ 371 (c)(1),
(2), (4) Date: Feb. 17, 2012

(87) PCT Pub. No.: WO2011/033837
PCT Pub. Date: Mar. 24, 2011

(65) Prior Publication Data
US 2012/0145910 A1    Jun. 14, 2012

(30) Foreign Application Priority Data

Sep. 18, 2009  (JP) ................................. 2009-217543

(51) Int. Cl.
*G01N 23/087* (2006.01)
*G01T 1/20* (2006.01)
*G01V 5/00* (2006.01)

(52) U.S. Cl.
CPC .............. *G01N 23/087* (2013.01); *G01V 5/005* (2013.01)
USPC ............ 250/370.11; 250/370.99; 250/370.08; 382/299; 378/98.9; 378/98.11; 378/98.12

(58) Field of Classification Search
CPC ........................... G01V 5/005; G01N 23/0087
USPC .............. 382/299; 378/19, 62, 91, 98.8, 98.9, 378/98.12, 98.11, 204, 210, 901, 53, 57; 250/370.01, 370.08, 370.09, 370.11, 250/371, 252.1
See application file for complete search history.

(56) References Cited

U.S. PATENT DOCUMENTS 4,109,152 A  8/1978 Aoki et al.
4,626,688 A  12/1986 Barnes
(Continued)

FOREIGN PATENT DOCUMENTS

EP       2 400 318       12/2011
(Continued)

OTHER PUBLICATIONS

Machine Translation of JP 2009-85627.*

*Primary Examiner* — Yara B Green
(74) *Attorney, Agent, or Firm* — Drinker Biddle & Reath LLP

(57) ABSTRACT

A radiation detection device 80 according to an embodiment is a radiation detection device for a foreign substance inspection using a subtraction method, and includes a first radiation detector 32 that detects radiation in a first energy range transmitted through a specimen S and generates a first image, a second radiation detector 42 that detects radiation in a second energy range higher than the radiation in the first energy range and generates a second image, a first image processing section 34 that applies image processing to the first image, and a second image processing section 44 that applies image processing to the second image, wherein a first pixel width in an image detection direction of each pixel of the first radiation detector 32 is smaller than a second pixel width in the image detection direction of each pixel of the second radiation detector 42, and the first image processing section 34 and the second image processing section 44 carry out pixel change processing to make the number of pixels of the first image and the number of pixels of the second image equal to each other.

16 Claims, 16 Drawing Sheets

(56) References Cited

U.S. PATENT DOCUMENTS

| | | | |
|---|---|---|---|
| 4,872,188 A | 10/1989 | Lauro et al. | |
| 5,878,108 A * | 3/1999 | Baba et al. | 378/98.4 |
| 6,002,810 A * | 12/1999 | Wakisawa et al. | 382/298 |
| RE37,536 E * | 2/2002 | Barnes | 250/361 R |
| 6,600,805 B2 * | 7/2003 | Hansen | 378/53 |
| 2002/0168046 A1* | 11/2002 | Hansen | 378/51 |
| 2004/0013224 A1* | 1/2004 | Baba et al. | 378/19 |
| 2005/0017184 A1 | 1/2005 | Groh et al. | |
| 2007/0057208 A1* | 3/2007 | Joss et al. | 250/559.19 |
| 2007/0114426 A1* | 5/2007 | Tkaczyk | 250/370.09 |
| 2008/0062174 A1* | 3/2008 | Wedel | 345/428 |
| 2010/0067822 A1* | 3/2010 | Young | 382/264 |

FOREIGN PATENT DOCUMENTS

| | | |
|---|---|---|
| JP | 61-143038 | 6/1986 |
| JP | 4-2907 | 1/1992 |
| JP | 5-68674 | 9/1993 |
| JP | 7-72257 | 3/1995 |
| JP | 2002-365368 | 12/2002 |
| JP | 2006-502386 | 1/2006 |
| JP | 2008-538966 | 11/2008 |
| JP | 2009-082250 | 4/2009 |
| JP | 2009-85627 | 4/2009 |
| JP | 2009-85844 | 4/2009 |
| JP | 2009-85845 | 4/2009 |
| JP | 2009-094902 | 4/2009 |
| JP | 2010-117170 | 5/2010 |
| JP | 2010-117172 | 5/2010 |
| JP | 2010-190830 | 9/2010 |
| JP | 2011-064643 | 3/2011 |
| TW | 200801571 | 1/2008 |
| TW | 200842393 | 11/2008 |

* cited by examiner

*Fig.3*
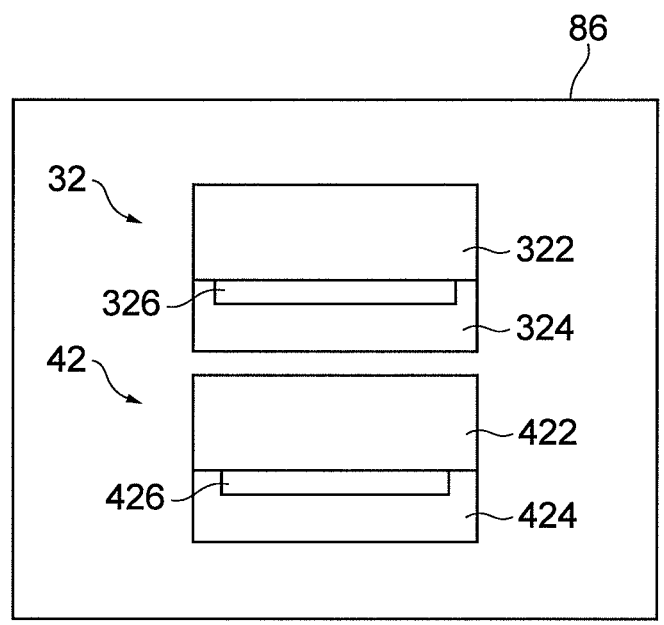
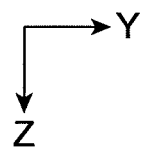

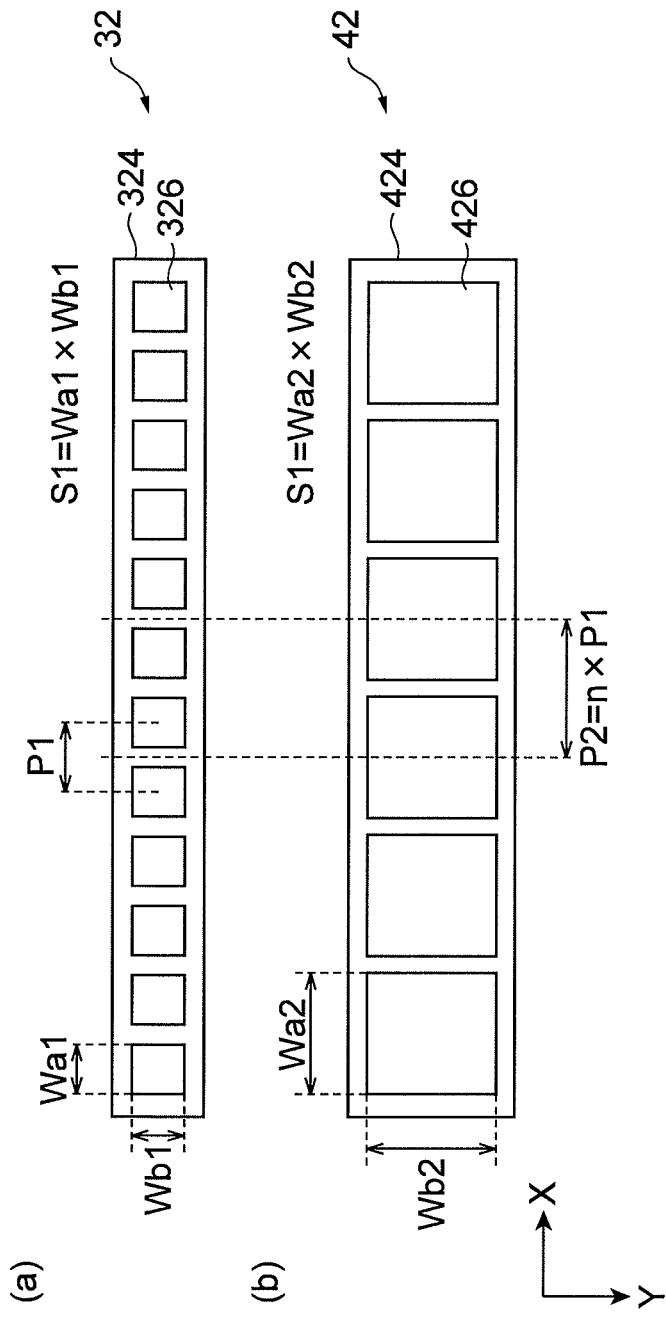

RADIATION DETECTING DEVICE

TECHNICAL FIELD

The present invention relates to a dual-energy radiation detection device.

BACKGROUND ART

Radiation detection devices that detect foreign substances, measure a component distribution, and measure weights, etc., in an in-line non-destructive inspection of a specimen that is conveyed by a belt conveyor or the like have been known. A radiation detection device includes a radiation detector having a scintillator layer and pixels, and detects radiation transmitted through a specimen and generates a radiation image.

This kind of radiation detection device is disclosed in Patent Literature 1. The radiation detection device described in Patent Literature 1 includes two radiation detectors with different pixel areas arranged side by side in a conveying direction of a belt conveyor. In this radiation detection device, large foreign substances are detected by the radiation detector with a larger pixel area, and small foreign substances are detected by the radiation detector with a smaller pixel area. By thus selecting a pixel size in advance according to a size of a foreign substance that a user desires to detect, foreign substance inspection accuracy can be improved.

As another method for improving the foreign substance inspection accuracy, a dual-energy radiation detection device has been known. A dual-energy radiation detection device includes two radiation detectors with different energy sensitivities, and detects radiation in a low-energy range (first energy range) and radiation in a high-energy range (second energy range) transmitted through a specimen. With this radiation detection device, a radiation image in a low-energy range and a radiation image in a high-energy range are simultaneously acquired, an image to which weighted subtraction and superimposition (for example, subtraction) is applied is created based on the radiation images, and according to a contrast difference in this image, a foreign substance is made to stand out, whereby realizing a foreign substance inspection with high accuracy.

CITATION LIST

Patent Literature

[Patent Literature 1] Japanese Patent Application Laid-Open No. 2009-85627

SUMMARY OF INVENTION

Technical Problem

For example, in an inspection of foreign substances in foods, it is required to carry out an inspection to detect bone, cartilage, and metal, etc., in meat as a foreign substance, and by utilizing the difference in radiation absorption between meat and a foreign substance (bone, cartilage, and metal, etc.), based on a contrast difference in a subtraction image of radiation images transmitted through these, a foreign substance is made to stand out, and accordingly, it is determined whether a foreign substance is present.

Here, bone and metal differ greatly in radiotransparency from (lower in radiotransparency than) meat, so that a contrast difference in at least a radiation image acquired with one of the radiation detectors is great. As a result, a contrast difference in a subtraction image of the two radiation images is great, so that a foreign substance inspection can be easily carried out. However, cartilage, like meat, has high radiotransparency, and a difference in radiotransparency between these is small, so that the contrast differences in radiation images acquired with the radiation detectors become small. As a result, a contrast difference in a subtraction image of these radiation images also becomes small, so that the foreign substance inspection is difficult.

In this regard, as a result of intensive study, the inventors of the present invention found that a contrast difference in a radiation image between lightweight atoms of meat and cartilage, etc., that is, between substances both having high radiotransparency could be made larger in a radiation image in a lower energy range. Further, the inventors of the present invention found that, when a charge amount to be converted by each pixel was reduced by reducing the areas of pixels in the radiation detector for low-energy range detection, a charge amount difference in a radiation image between substances both having high radiotransparency could be made relatively large, and a contrast difference in a radiation image of these could be increased.

However, to reduce the areas of pixels in the low energy radiation detector, if the pixel width in the pixel array direction (image detection direction) is made smaller and the number of pixels increases, the number of pixels output from the low energy radiation detector and the number of pixels output from the high energy radiation detector are different from each other, and as a result, it becomes difficult to carry out subtraction processing, that is, it becomes difficult to carry out difference processing.

Therefore, an object of the present invention is to provide a radiation detection device that can easily carry out arithmetic processing based on radiation images acquired with two radiation detectors even when the radiation detectors have a different number of pixels.

Solution to Problem

A radiation detection device according to the present invention is a radiation detection device for a foreign substance inspection using a subtraction method, which detects radiation in a first energy range and radiation in a second energy range higher than the radiation in the first energy range that are transmitted through a specimen and incident from a radiation incident direction, comprising: a first radiation detector that is positioned on the upstream side with respect to the radiation incident direction, and detects radiation in the first energy range and generates a first image corresponding to an image of the radiation; a second radiation detector that is positioned on the downstream side with respect to the radiation incident direction, and detects radiation in the second energy range and generates a second image corresponding to an image of the radiation; a first image processing section that applies image processing to the first image from the first radiation detector; and a second image processing section that applies image processing to the second image from the second radiation detector. The first radiation detector includes a first pixel section that has a plurality of pixels arrayed along an image detection direction and acquires the first image based on the image of the radiation in the first energy range, and the second radiation detector includes a second pixel section that has a plurality of pixels arrayed along the image detection direction and acquires the second image based on the image of the radiation in the second energy range. A first pixel width in the image detection direction of each of the plurality of pixels in the first pixel section is smaller than a second pixel width in the image detection direction of each of the plurality of pixels in the second pixel section, and the first image processing section and the second image processing section carry out pixel change processing to make the number of pixels of the first image and the number of pixels of the second image equal to each other.

When using a subtraction method, the two radiation detectors are required to image spatially and temporally the same position on a specimen. Therefore, with the type including two radiation detectors arranged side by side as described in Patent Literature 1, the detection timings of the radiation detectors must be adjusted. Even after the detection timings are adjusted, it is still difficult for the radiation detectors to image the same position, that is, exactly the same area in a specimen, so that position accuracy may become low. Thus, if a subtraction image in which the ends of the detection areas partially deviate from each other is created, pseudo edges such as a bright edge (white edge) and a dark edge (black edge) may be formed at an end portion of the detected object in the subtraction image.

On the other hand, in this radiation detection device, the first radiation detector and the second radiation detector are disposed so as to overlap in the radiation incident direction, that is, the radiation detection device is a vertically-piled type, so that the radiation detectors can easily image temporally the same position on a specimen without detection timing control simultaneously.

With this radiation detection device, even when the first pixel width of the pixel in the image detection direction in the first radiation detector is smaller than the second pixel width of the pixel in the image detection direction in the second radiation detector, that is, even when the number of pixels in the first radiation detector and the number of pixels in the second radiation detector are different from each other, the first image processing section and the second image processing section carry out pixel change processing to make the number of pixels of a first image from the first radiation detector and the number of pixels of a second image from the second radiation detector equal to each other so that the pixels of the first image from the first radiation detector and the pixels of the second image from the second radiation detector correspond to each other, so that arithmetic processing based on the radiation image acquired with the first radiation detector and the radiation image acquired with the second radiation detector, for example, subtraction processing can be easily carried out.

The above-described first image processing section and second image processing section may apply pixel thinning-out processing to at least one of the number of pixels of the first image and the number of pixels of the second image, or may apply pixel interpolation processing to at least one of the number of pixels of the first image and the number of pixels of the second image.

As the above-described thinning-out processing, simple thinning-out processing, averaging thinning-out processing, summing thinning-out processing, minimum filter thinning-out processing, or maximum filter thinning-out processing is applicable, and as the above-described interpolation processing, simple interpolation processing, primary interpolation processing, secondary interpolation processing, spline interpolation processing, or Lagrange interpolation processing is applicable.

In the above-described thinning-out processing, it is possible that, based on a ratio of J to K of the number of pixels of the first image to the number of pixels of the second image, one correction pixel is generated from two pixels adjacent to each other of at least one of the pixels of the first image and the pixels of the second image so that the number of pixels of the first image becomes 1/J and the number of pixels of the second image becomes 1/K, and a brightness value $IL(y)$ of the corrected image is set to satisfy the following equation:

$$IL(y)=\gamma(\alpha \times L(x)+\beta \times L(x+1))$$

based on signal values $L(x)$ and $L(x+1)$ of the two pixels before being corrected, pixel correction factors $\alpha$ and $\beta$, and a brightness adjustment factor $\gamma$.

In the above-described interpolation processing, based on the ratio J to K of the number of pixels of the first image to the number of pixels of the second image and a least common multiple L of J and K, an interpolation pixel is interpolated for at least one of among the pixels of the first image and among the pixels of the second image so that the number of pixels of the first image becomes L/J and the number of pixels of the second image becomes L/K, and a brightness value $IH(y)$ of the interpolation pixel is set to satisfy the following equation:

$$IH(y)=\gamma(\alpha \times H(x)+\beta \times H(x+1))$$

based on signal values $H(x)$ and $H(x+1)$ of the pixels adjacent to both sides of the interpolation pixel, pixel correction factors $\alpha$ and $\beta$, and a brightness adjustment factor $\gamma$.

The above-described first radiation detector may include a first scintillator layer that extends along the image detection direction and converts an image of radiation in the first energy range into an optical image, and a first pixel section that acquires a first image based on an optical image converted by the first scintillator layer, and the above-described second radiation detector may include a second scintillator layer that extends along the image detection direction and converts an image of radiation in the second energy range into an optical image, and a second pixel section that acquires a second image based on an optical image converted by the second scintillator layer.

Advantageous Effects of Invention

According to the present invention, in a dual-energy radiation detection device using a subtraction method, even when the number of pixels of two radiation detectors are different from each other, arithmetic processing, for example, subtraction processing based on radiation images acquired with these radiation detectors can be easily carried out.

BRIEF DESCRIPTION OF DRAWINGS

FIG. 3 is a schematic structural drawing of a dual-energy sensor in a radiation detection device according to an embodiment of the present invention.

FIG. 16 is a drawing showing X-ray incidence planes of a low energy detector and a high energy detector in a dual-energy sensor according to an exemplary variation of the present invention.

DESCRIPTION OF EMBODIMENTS

Figure 1:
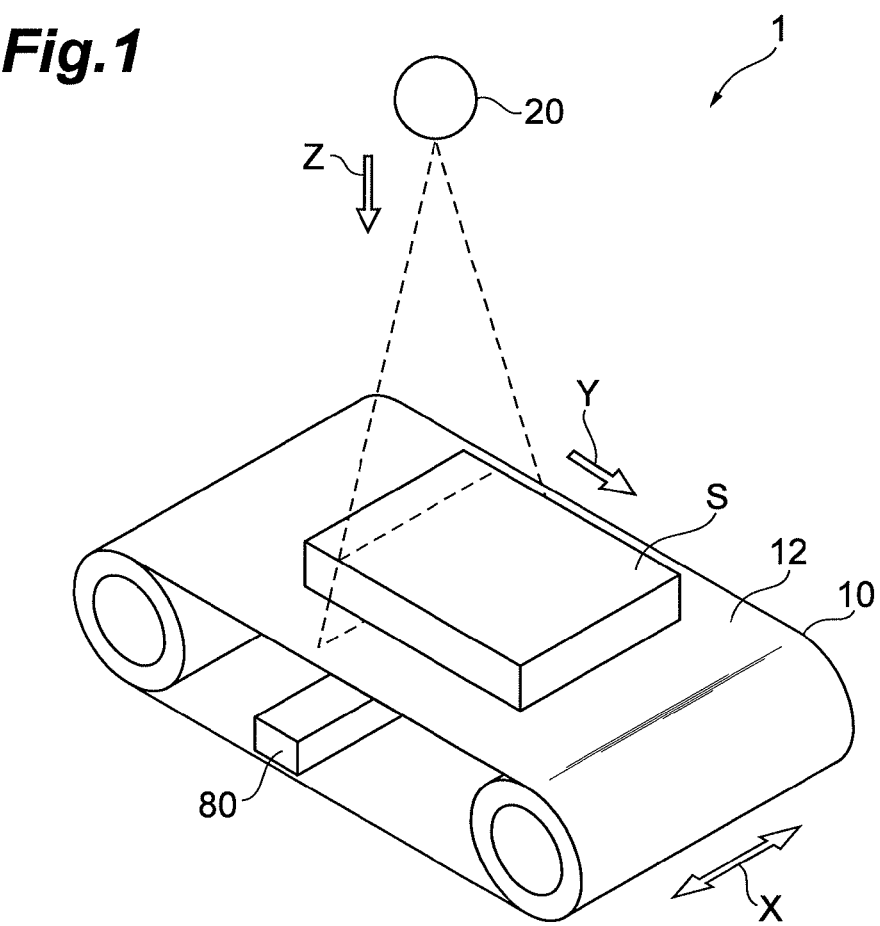
FIG. 1 is a perspective view of an X-ray foreign substance inspection device according to the present embodiment.

Hereinafter, a preferred embodiment of the present invention is described with reference to the drawings. In the drawings, portions identical to or equivalent to each other are designated by the same reference signs.

Figure 2:
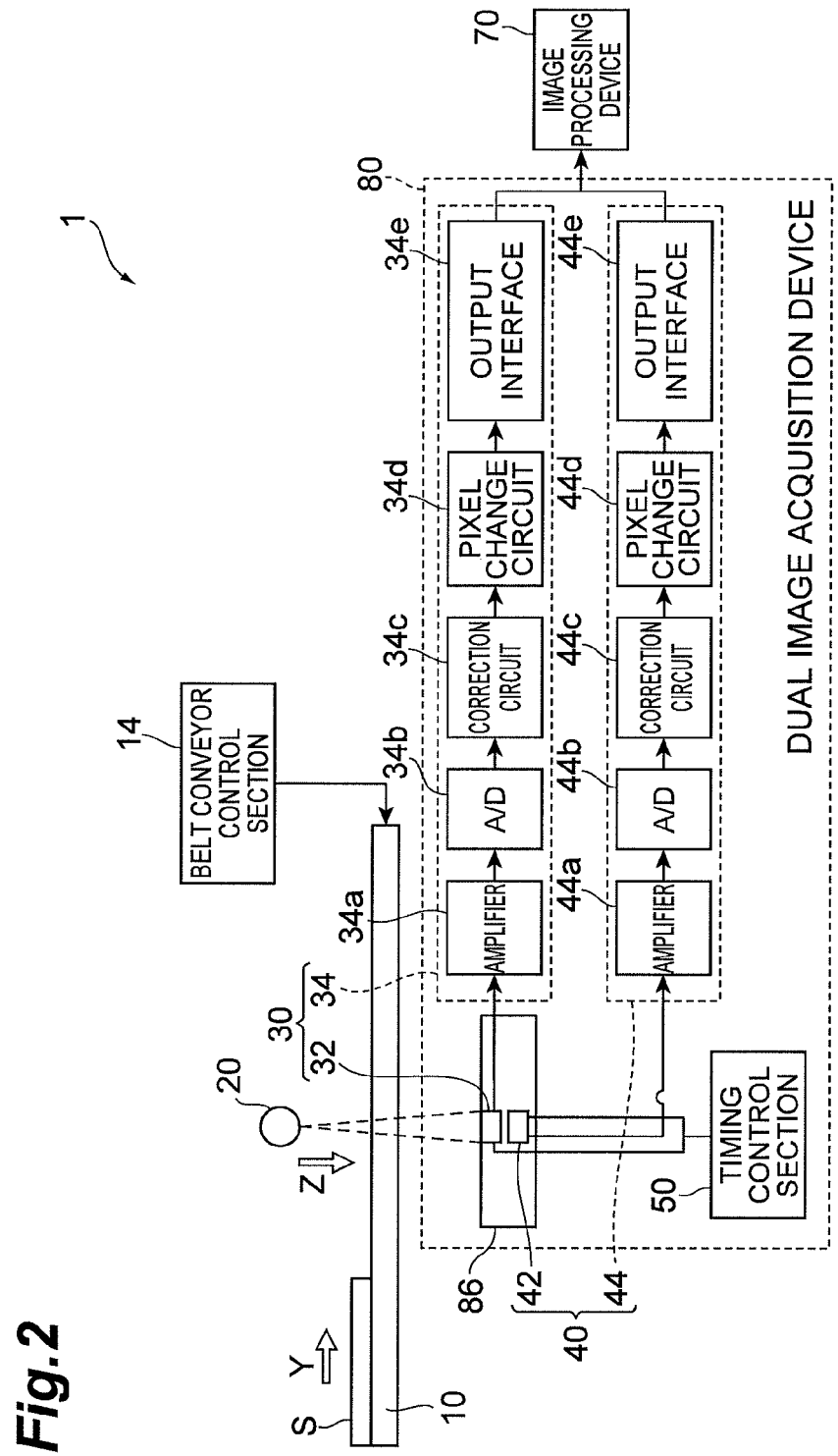
FIG. 2 is a schematic configuration view of the X-ray foreign substance inspection device according to the present embodiment.

FIG. 1 is a perspective view of an X-ray foreign substance inspection device according to the present embodiment, and FIG. 2 is a schematic configuration view of the X-ray foreign substance inspection device according to the present embodiment. As shown in FIG. 1 and FIG. 2, the X-ray foreign substance inspection device 1 irradiates X-rays (radiation) from an X-ray source onto a specimen S in an irradiation direction Z, and detects transmitted X-rays transmitted through the specimen S of the irradiated X-rays in a plurality of energy ranges. The X-ray foreign substance inspection device 1 carries out a foreign substance inspection and a baggage inspection for inspecting foreign substances included in a specimen S by using transmitted X-ray images. Such an X-ray foreign substance inspection device 1 includes a belt conveyor 10, an X-ray irradiator 20, a low energy image acquisition section 30, a high energy image acquisition section 40, a timing control section 50, and an image processing device 70. The low energy image acquisition section 30, the high energy image acquisition section 40, and the timing control section 50 constitute a dual-energy radiation detection device 80 according to an embodiment of the present invention.

The belt conveyor 10 includes a belt portion 12 on which a specimen S is placed as shown in FIG. 1. The belt conveyor 10 conveys the specimen S in a conveying direction Y at a predetermined conveying speed by moving the belt portion 12 in the conveying direction Y The conveying speed of the specimen S is, for example, 48 m/min. The belt conveyor 10 can change the conveying speed to, for example, 24 m/min and 96 m/min by the belt conveyor control section 14 as appropriate. The belt conveyor control section 14 can change the height position of the belt portion 12. By changing the height position of the belt portion 12, the distance between the X-ray irradiator 20 and the specimen S can be changed. By this change, the resolution of X-ray transmitted images to be acquired with the low energy image acquisition section 30 and the high energy image acquisition section 40 can be changed. The specimen S to be conveyed by the belt conveyor 10 is composed of various objects, for example, foods such as meat, rubber products such as tires, baggage and cargo to be subjected to baggage inspections and cargo inspections for security and safety, and other resin products and metal products, resource materials such as mineral substances, waste to be separated and collected (recycled) as resources, and electronic components, etc.

The X-ray irradiator 20 is an X-ray source that irradiates X-rays in the irradiation direction Z onto the specimen S. The X-ray irradiator 20 is a point light source, and diffuses and irradiates X-rays in a predetermined angle range in a detection direction X orthogonal to the irradiation direction Z and the conveying direction Y. The X-ray irradiator 20 is disposed above the belt portion 12 at a predetermined distance to the belt portion 12 so that the X-ray irradiation direction Z is directed toward the belt portion 12 and X-rays diffuse to the entirety in the width direction (detection direction X) of the specimen S. The X-ray irradiator 20 has an irradiation range set to a predetermined divided region in the longitudinal direction (conveying direction Y) of the specimen S, and by conveying the specimen S in the conveying direction Y by the belt conveyor 10, X-rays are irradiated onto the entirety in the longitudinal direction of the specimen S.

The low energy image acquisition section 30 includes a low energy detector (first radiation detector) 32 and a low energy image correction section (first image processing section) 34.

The low energy detector 32 is positioned on the upstream side with respect to the X-ray incident direction Z, and detects X-rays in a low-energy range (first energy range) transmitted through the specimen S of the X-rays irradiated from the X-ray irradiator 20 and generates low energy image data (first radiation image data).

The low energy image correction section 34 amplifies, corrects, and changes low energy image data generated by the low energy detector 32. The low energy image correction section 34 includes an amplifier 34a that amplifies low energy image data, an A/D converter 34b that A/D converts the low energy image data amplified by the amplifier 34a, a correction circuit 34c that applies predetermined correction processing to the low energy image data converted by the A/D converter 34b, a pixel change circuit 34d that changes the number of pixels of the image data corrected by the correction circuit 34c, and an output interface 34e that outputs the image data changed by the pixel change circuit 34d to the outside. The details of the pixel change circuit 34d will be described later.

The high energy image acquisition section 40 includes a high energy detector (second radiation detector) 42 and a high energy image correction section (second image processing section) 44.

The high energy detector 42 is positioned on the downstream side with respect to the X-ray incident direction Z, and detects X-rays in a high-energy range (second energy range) transmitted through the specimen S and the low energy detector 32 of the X-rays irradiated from the X-ray irradiator 20 and generates high energy image data (second radiation image data). The low-energy range detected by the low energy detector 32 and the high-energy range detected by the high energy detector 42 are not clearly discriminated from each other, but overlap to some extent.

The high energy image correction section 44 amplifies, corrects, and changes high energy image data generated by the high energy detector 42. The high energy image correction section 44 includes an amplifier 44a that amplifies high energy image data, an A/D converter 44b that A/D converts high energy image data amplified by the amplifier 44a, a correction circuit 44c that applies predetermined correction processing to the high energy image data converted by the A/D converter 44b, a pixel change circuit 44d that changes the number of pixels of the image data corrected by the correction circuit 44c, and an output interface 44e that outputs image data changed by the pixel change circuit 44d to the outside. The details of the pixel change circuit 44d will be described later.

The timing control section 50 controls transmitted X-ray detection timings in the low energy detector 32 and transmitted X-ray detection timings in the high energy detector 42. The timing control section 50 reduces an image deviation in the following subtraction processing by making low energy image data and high energy image data correspond to each other.

The image processing device 70 is a device that generates a subtraction image as a synthesized image by carrying out arithmetic processing (subtraction processing) for calculating difference data between low energy image data detected and generated by the low energy detector 32 and high energy image data detected and generated by the high energy detector 42. The detection timings of both energy image data to be input into the image processing device 70 are controlled by the timing control section 50 so that both image data correspond to each other. The image processing device 70 outputs the subtraction image generated by the arithmetic processing to a display, etc., and displays it thereon. By this output display, foreign substances, etc., included in the specimen S can be visually confirmed. It is also possible that the subtraction image is not output and displayed but only data is output so that foreign substances, etc., included in the specimen S are directly detected from the image data by detection processing on the image data.

Next, the low energy detector 32 and the high energy detector 42 are described in detail. FIG. 3 is a schematic structural drawing of a dual-energy sensor 86 consisting of the low energy detector 32 and the high energy detector 42 in the radiation detection device 80 shown in FIG. 2, and FIG. 4 is a drawing showing an X-ray incidence plane (a) of the low energy detector 32 and an X-ray incidence plane (b) of the high energy detector 42.

Figure 4:
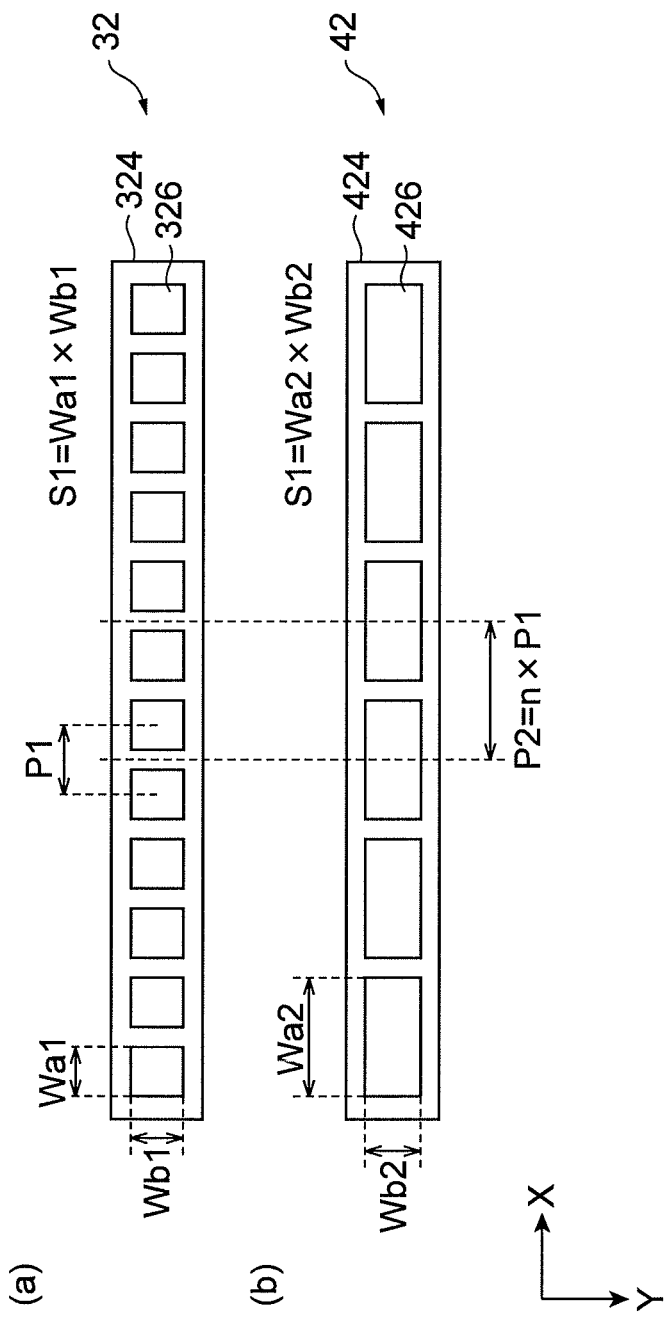
FIG. 4 is a drawing showing X-ray incidence planes of a low energy detector and a high energy detector in the dual-energy sensor shown in FIG. 3.

As shown in FIG. 3 and FIG. 4, the low energy detector 32 includes a low energy scintillator layer (first scintillator layer) 322 and a low energy line sensor (first pixel section) 324. The low energy scintillator layer 322 extends along the image detection direction X and converts an image of X-rays in the low-energy range into an optical image. The low energy line sensor 324 includes a plurality of pixels 326 arrayed along the image detection direction X, and acquires a low energy image (first image) based on the optical image converted by the low energy scintillator layer 322. Thus, the low energy detector 32 detects X-rays in the low-energy range.

Similarly, the high energy detector 42 includes a high energy scintillator layer (second scintillator layer) 422 and a high energy line sensor (second pixel section) 424. The high energy scintillator layer 422 extends along the image detection direction X and converts an image of X-rays in the high-energy range into an optical image. The high energy line sensor 424 includes a plurality of pixels 426 arrayed along the image detection direction X, and acquires a high energy image (second image) based on the optical image converted by the high energy scintillator layer 422. The high energy detector 42 thus detects X-rays in the high-energy range.

Here, the pixel width (first image detection direction width) Wa1 in the image detection direction X of each of the plurality of pixels 326 in the low energy line sensor 324 is smaller than the pixel width (second image detection direction width) Wa2 in the image detection direction X of each of the plurality of pixels 426 in the high energy line sensor 424. On the other hand, the pixel width (first orthogonal direction width) Wb1 in an orthogonal direction (conveying direction Y) orthogonal to the image detection direction X of each of the plurality of pixels 326 in the low energy line sensor 324 is equal to the pixel width (second orthogonal direction width) Wb2 in the orthogonal direction Y of each of the plurality of pixels 426 in the high energy line sensor 424. Thus, the area (first area) S1 of each of the plurality of pixels 326 in the low energy line sensor 324 is smaller than the area (second area) S2 of each of the plurality of pixels 426 in the high energy line sensor 424. The number of pixels per unit length of the high energy line sensor 424 and the number of pixels per unit length of the low energy sensor 342 are different from each other, and the number of pixels in the low energy line sensor 324 is larger than the number of pixels in the high energy line sensor 424.

The pixel pitch P2 of the pixels 426 in the high energy line sensor 424 is n times (n is a positive number) as large as the pixel pitch P1 of the pixels 326 in the low energy line sensor 324.

The material of the low energy scintillator layer 322 and the material of the high energy scintillator layer 422 may be the same, or may be different from each other. For example, as materials of the low energy scintillator layer 322 and the high energy scintillator layer 422, $Gd_2O_2S$: Tb, CsI: T1, $CdWO_4$, $CaWO_4$, GSO, LGSO, BGO, LSO, YSO, YAP, $Y_2O_2S$: Tb, $YTaO_4$: Tm, etc., are applicable, and a combination of materials is selected according to X-rays to be detected. The low energy detector 32 and the high energy detector 42 may be X-ray detectors having an energy discrimination function using a direct conversion system of CdTe (cadmium telluride), etc.

Here, in a foreign substance inspection in foods, it is required to carry out the inspection to detect bone, cartilage, and metal, etc., in meat as a foreign substance, and by utilizing the difference in radiation absorption between meat and a foreign substance (bone, cartilage, and metal, etc.), a foreign substance is made to stand out due to contrast differences in a subtraction image of radiation images transmitted through these, and it is determined whether a foreign substance is present.

Here, bone and metal differ greatly in radiotransparency from (lower than) that of meat, so that a contrast difference in at least a radiation image acquired with one of the radiation detectors is great. As a result, a contrast difference in a subtraction image of two radiation images is great, so that a foreign substance inspection is easily carried out. However, cartilage, like meat, has high radiotransparency, and the difference in radiotransparency between these is small, so that contrast differences in radiation images acquired with both radiation detectors become small. As a result, a contrast difference in a subtraction image of these radiation images is also small, so that a foreign substance inspection was difficult.

However, in the low energy detector 32 that detects a radiation image in the low-energy range, which can make a contrast difference in a radiation image between lightweight atoms of meat and cartilage, etc., that is, between substances both having high radiotransparency comparatively large, when the pixel width Wa1 in the detection direction X of each pixel 326 is made smaller, that is, the area S1 of each pixel 326 in the low energy detector 32 is made smaller, a charge amount to be converted by each pixel 326 becomes smaller, and a charge amount difference in a radiation image between lightweight atoms of meat and cartilage, etc., that is, between substances both having high radiotransparency, can be made relatively large, and a contrast difference in a radiation image of these can be made larger. As a result, a foreign substance inspection can be easily carried out.

Next, the pixel change circuit 34*d* in the low energy image correction section 34 and the pixel change circuit 44*d* in the high energy image correction section 44 are described in detail.

Figure 5:
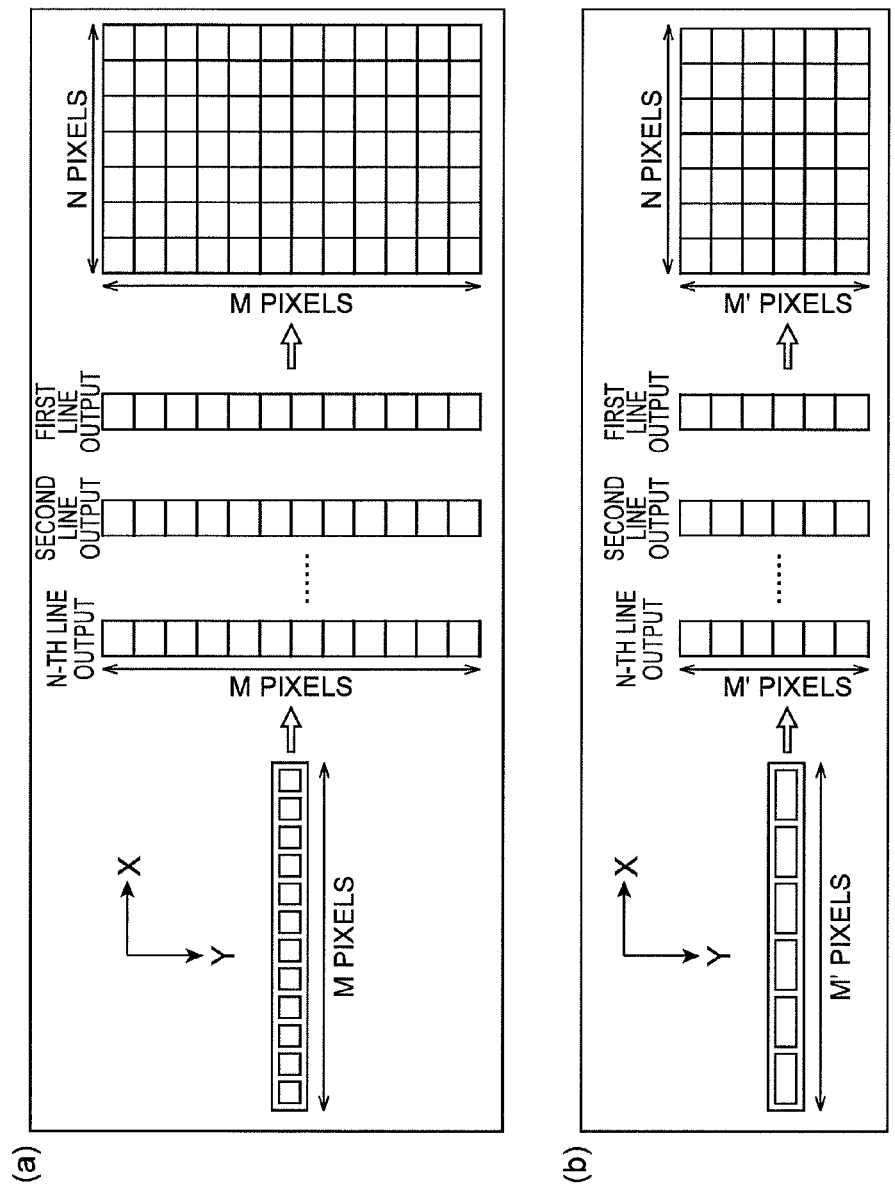
FIG. 5 is a conceptual diagram showing image processings in a low energy image correction section and a high energy image correction section shown in FIG. 2.

FIG. 5 is a conceptual diagram showing image processing (a) by the low energy image correction section 34 and image processing (b) by the high energy image correction section 44.

As shown in FIG. 5(*a*), the number of pixels of an image output from the low energy detector 32 becomes M×N as a result of two-dimensional image processing applied to the M pixels (in the detection direction X) and N line outputs (in the conveying direction Y). On the other hand, referring to FIG. 5(*b*), the number of pixels of an image output from the high energy detector 42 becomes M'×N (M'<M) as a result of two-dimensional image processing applied to M' pixels (in the detection direction X)×N line outputs (in the conveying direction Y).

Thus, when the pixel area S1 of the low energy detector 32 and the pixel area S2 of the high energy detector 42 are different from each other, that is, when the pixel width Wa1 in the detection direction X of the low energy detector 32 and the pixel width Wa2 in the detection direction X of the high energy detector 42 are different from each other, the number of pixels M per one line output in an image output from the low energy detector 32 and the number of pixels M' per one line output in an image output from the high energy detector 42 are different from each other, and it is difficult to create a subtraction image by carrying out difference processing of these.

Therefore, the pixel change circuits 34*d* and 44*d* carry out pixel change processing to make equal the number of pixel M of the image from the low energy detector 32 and the number of pixels M' of the image from the high energy detector 42 to each other. As this pixel change processing, pixel interpolation processing and pixel thinning-out processing, etc., are applicable.

(1) Pixel Interpolation Processing

First, pixel interpolation processing is described in detail. In the pixel interpolation processing, pixel interpolation is carried out to adjust the number of pixels M' of the image from the high energy detector 42 to the number of pixels M of the image from the low energy detector 32. As this pixel interpolation processing, examples of simple interpolation processing and primary interpolation processing are described below.

(1-1) Simple Interpolation Processing

Figure 6:
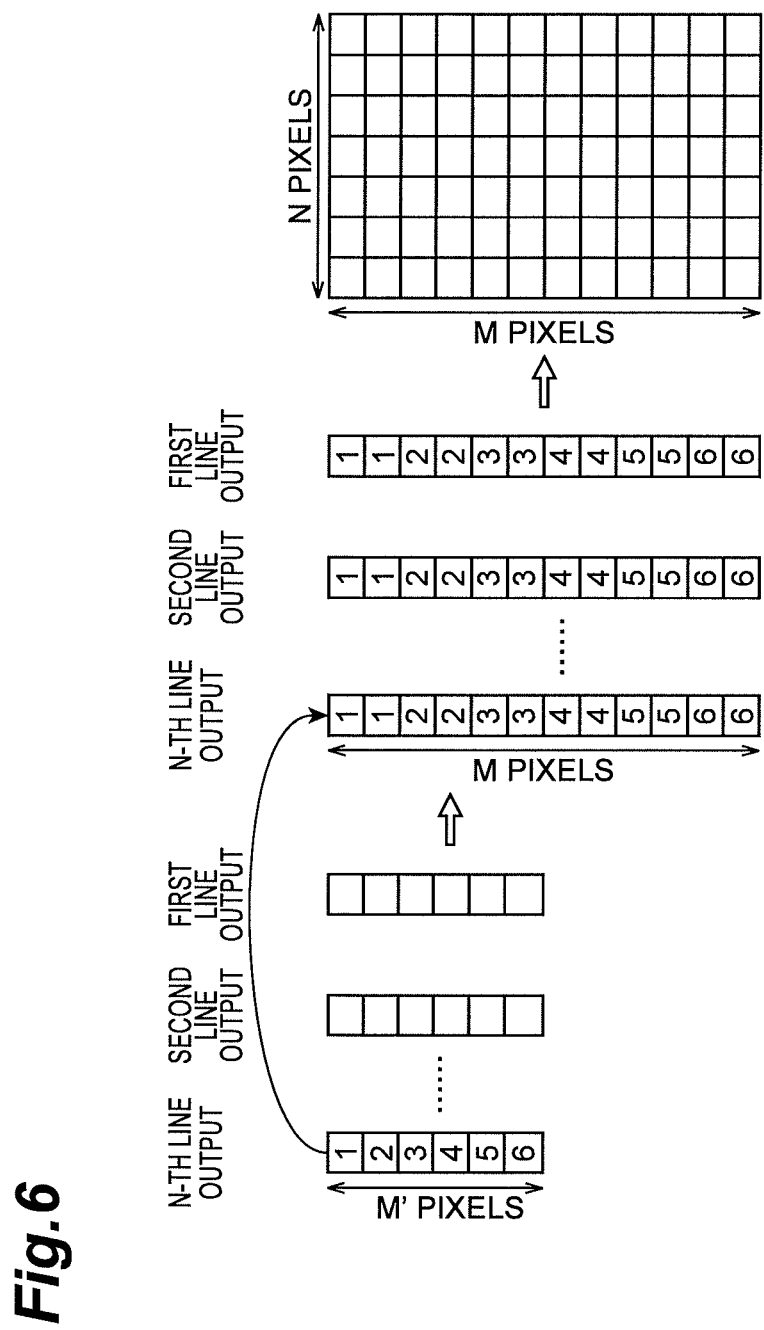
FIG. 6 is a conceptual diagram showing an example of simple interpolation processing.

FIG. 6 is a conceptual diagram showing an example of simple interpolation processing. In this simple interpolation processing, by the pixel change circuit 44*d*, interpolation pixels that are simple copies of the pixels in the image output from the high energy detector 42 are generated and interpolated so as to become adjacent to corresponding pixels. At this time, the pixel change circuit 34*d* outputs the image output from the low energy detector 32 as it is without applying this simple interpolation processing thereto.

(1-2) Primary Interpolation Processing

Figure 7:
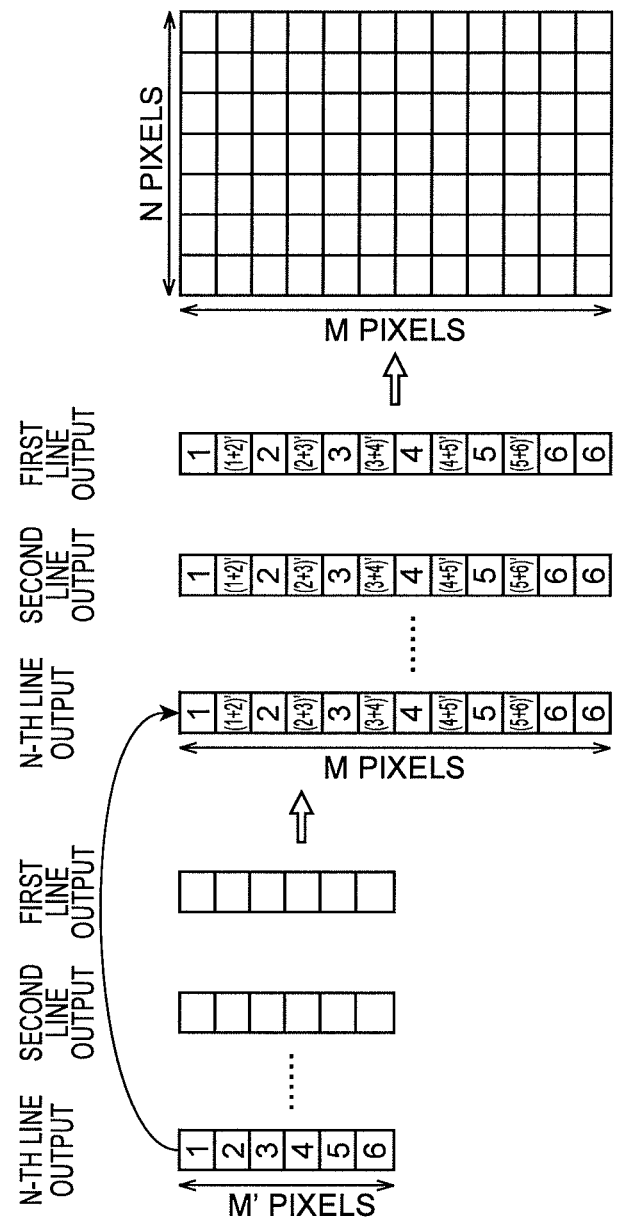
FIG. 7 is a conceptual diagram showing an example of primary interpolation processing.

FIG. 7 is a conceptual diagram showing an example of primary interpolation processing. In this primary interpolation processing, the pixel change circuit 44*d* generates an interpolation pixel with an average brightness of pixels adjacent to each other in the image output from the high energy detector 42, and interpolates the interpolation pixel between the adjacent pixels. For example, a (1+2)'-th pixel is interpolated between the first pixel and the second pixel. The brightness value of the (1+2)'-th pixel is calculated according to the following equation:

[brightness value of (1+2)'-th pixel]=[brightness value of first pixel]+[brightness value of second pixel]/2

In this case, the pixel change circuit 34*d* outputs the image output from the low energy detector 32 as it is without applying this primary interpolation processing thereto.

Here, this primary interpolation processing is generalized. For example, when the ratio of the number of pixels of the image from the low energy detector 32 to the number of pixels of the image from the high energy detector 42 is 2 to 1, the pixel change circuit 44*d* carries out interpolation processing based on this ratio so as to double the number of pixels of the image from the high energy detector 42. Specifically, one interpolation pixel is interpolated each between the pixels. Next, when the ratio of the number of pixels of the image from the low energy detector 32 to the number of pixels of the image from the high energy detector 42 is 3 to 1, the pixel change circuit 44*d* carries out the interpolation processing based on this ratio so as to triple the number of pixels of the image from the high energy detector 42. Specifically, two pixels are interpolated each between the pixels. Next, in a case where the ratio of the number of pixels of the image from the low energy detector 32 to the number of pixels of the image from the high energy detector 42 is 4 to 3, the pixel change circuit 44*d* interpolates three interpolation pixels each between the pixels so as to quadruple the number of pixels of the image from the high energy detector 42. In addition, the pixel change circuit 34*d* interpolates two interpolation pixels each between the pixels so as to triple the number of pixels of the image from the low energy detector 32.

Based on this, generalizing the primary interpolation processing, when the ratio of the number of pixels of the image from the low energy detector 32 to the number of pixels of the image from the high energy detector 42 is J to K, a least common multiple L of J and K is calculated, and the pixel change circuit 34*d* interpolates interpolation pixels so as to increase the number of pixels of the image from the low energy detector 32 L/J times, and the pixel change circuit 44*d* interpolates interpolation pixels so as to increase the number of pixels of the image from the high energy detector 42 L/K times.

Then, the brightness values of these interpolation pixels are calculated as follows. When H(x) and H(x+1) are signals of pixels adjacent to each other to be subjected to interpolation, and interpolation is applied between the pixels of H(x) and H(x+1), a brightness value IH(y) of an interpolation pixel is expressed by the following equation:

$$IH(y)=\gamma(\alpha \times H(x)+\beta \times H(x+1))$$

Here, $\alpha$ is a leading pixel correction factor, $\beta$ is a following pixel correction factor, $\gamma$ is a brightness adjustment factor, and x indicates the order of pixels to be subjected to interpolation. $\alpha$ and $\beta$ may be arbitrary numbers, or may be calculated. Alternatively, constants may also be used.

According to this generalization, for example, when $\alpha=1$, $\beta=0$, and $\gamma=1$, the above-described simple interpolation processing is applied.

Figure 8:
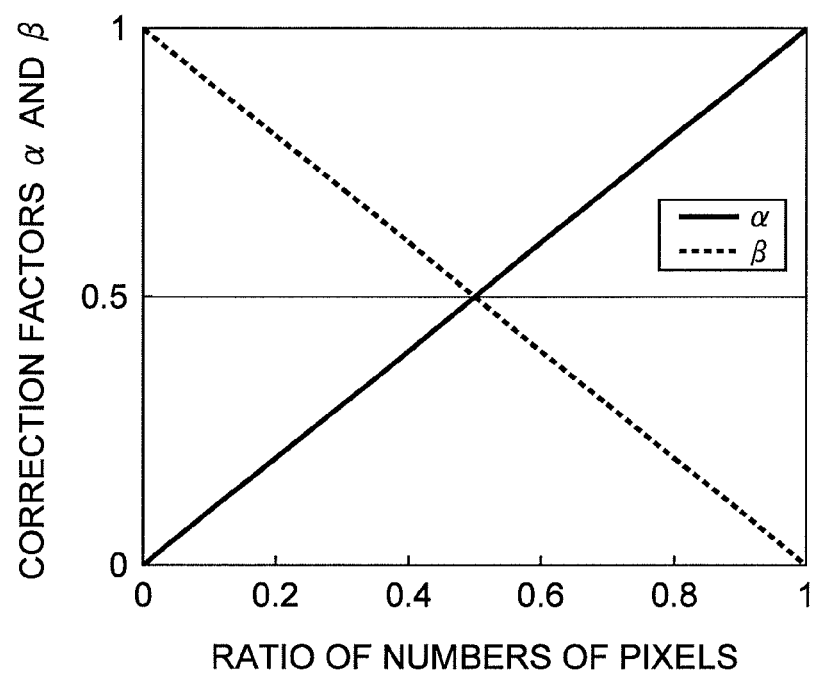
FIG. 8 is a diagram showing correction factors with respect to a ratio of the numbers of pixels for brightness calculation of an interpolation pixel.

The correction factors $\alpha$ and $\beta$ may be calculated according to the number of interpolation pixels as shown in FIG. 8. For example, when the ratio of the number of pixels of the image from the low energy detector 32 to the number of pixels of the image from the high energy detector 42 is 2 to 1 and only one pixel is interpolated, $\alpha$ and $\beta$ are calculated as $\alpha=0.5$ and β=0.5 from FIG. 8. This is calculation of an average of two pixels. When the ratio of the number of pixels of the image from the low energy detector 32 to the number of pixels of the image from the high energy detector 42 is 4 to 1 and three pixels are interpolated, in order from the H(x) side of FIG. 8, for a first interpolation pixel, α=0.75 and β=0.25, for a second interpolation pixel, α=0.5 and β=0.5, and for a third interpolation pixel, α=0.25 and β=0.75. Thus, the brightness value of a correction pixel between two pixels may be calculated according to the ratio of the number of pixels, that is, the number of interpolation pixels.

At an end of an image, pixels to be subjected to interpolation may be insufficient, and in this case, α=1 and β=0 are set and simple interpolation is carried out.

Pixel interpolation processing is not limited to the above-described simple interpolation processing and primary interpolation processing, but various methods are applicable. For example, various methods such as an interpolation method using a secondary interpolation method, an interpolation method using a spline interpolation method, and an interpolation method using a Lagrange interpolation method, may be adopted. The Lagrange interpolation method is a method in which a curve passing through all of n+1 points is derived by creating an n-order function when n+1 points are given, and mean brightness values are interpolated by using the curve.

(2) Pixel Thinning-Out Processing

Next, pixel thinning-out processing is described in detail. In pixel thinning-out processing, pixel thinning-out is carried out so that the number of pixels M of the low energy detector 32 is adjusted to the number of pixels M' of the high energy detector 42. As this pixel thinning-out processing, examples of simple thinning-out processing, averaging thinning-out processing, summing thinning-out processing, and minimum filter thinning-out processing are described below.

(2-1) Simple Thinning-Out Processing

Figure 9:
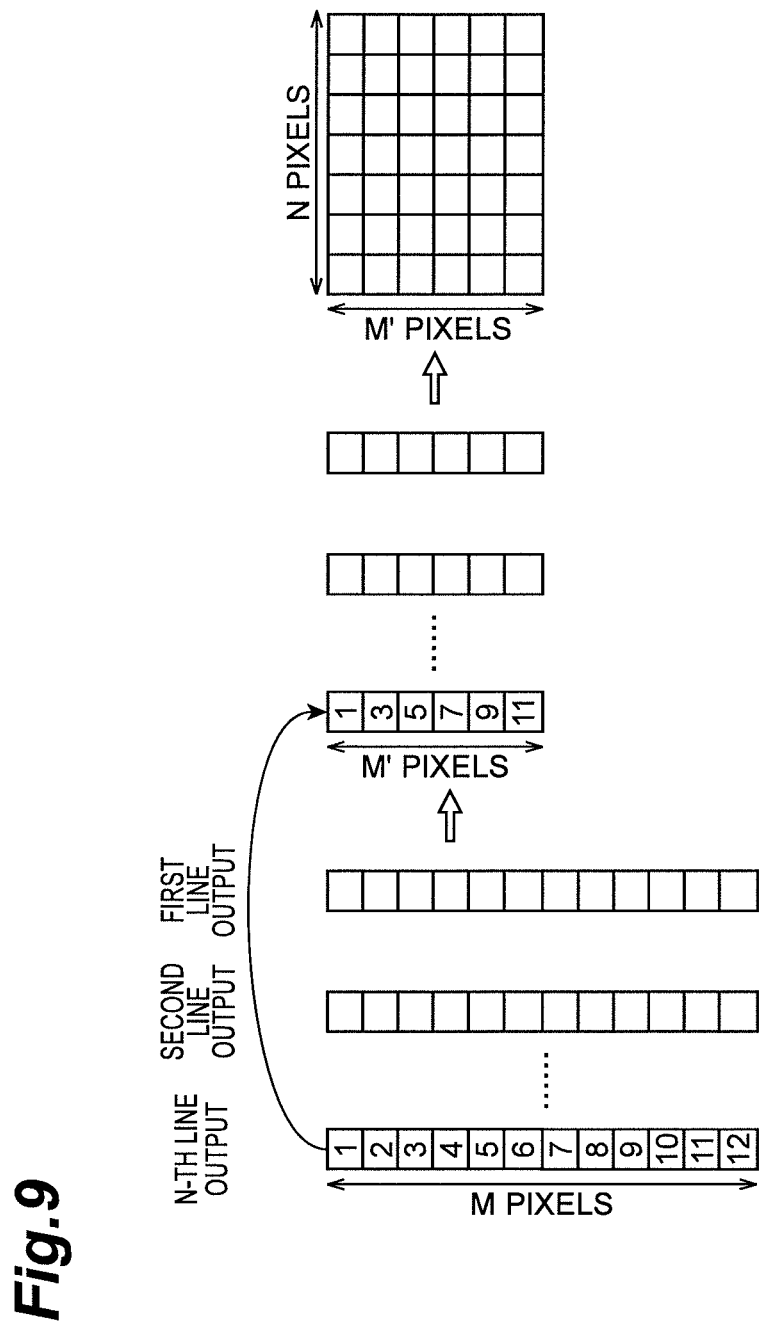
FIG. 9 is a conceptual diagram showing an example of simple thinning-out processing.

FIG. 9 is a conceptual diagram showing an example of simple thinning-out processing. In this simple thinning-out processing, by the pixel change circuit 34d, thinning-out is carried out by removing odd-numbered or even-numbered pixels of pixels adjacent to each other in the image output from the low energy detector 32. For example, in FIG. 9, odd-numbered pixels are left and even-numbered pixels are removed. In this case, the pixel change circuit 44d outputs the image output from the high energy detector 42 as it is without applying this simple thinning-out processing thereto.

(2-2) Averaging Thinning-Out Processing

Figure 10:
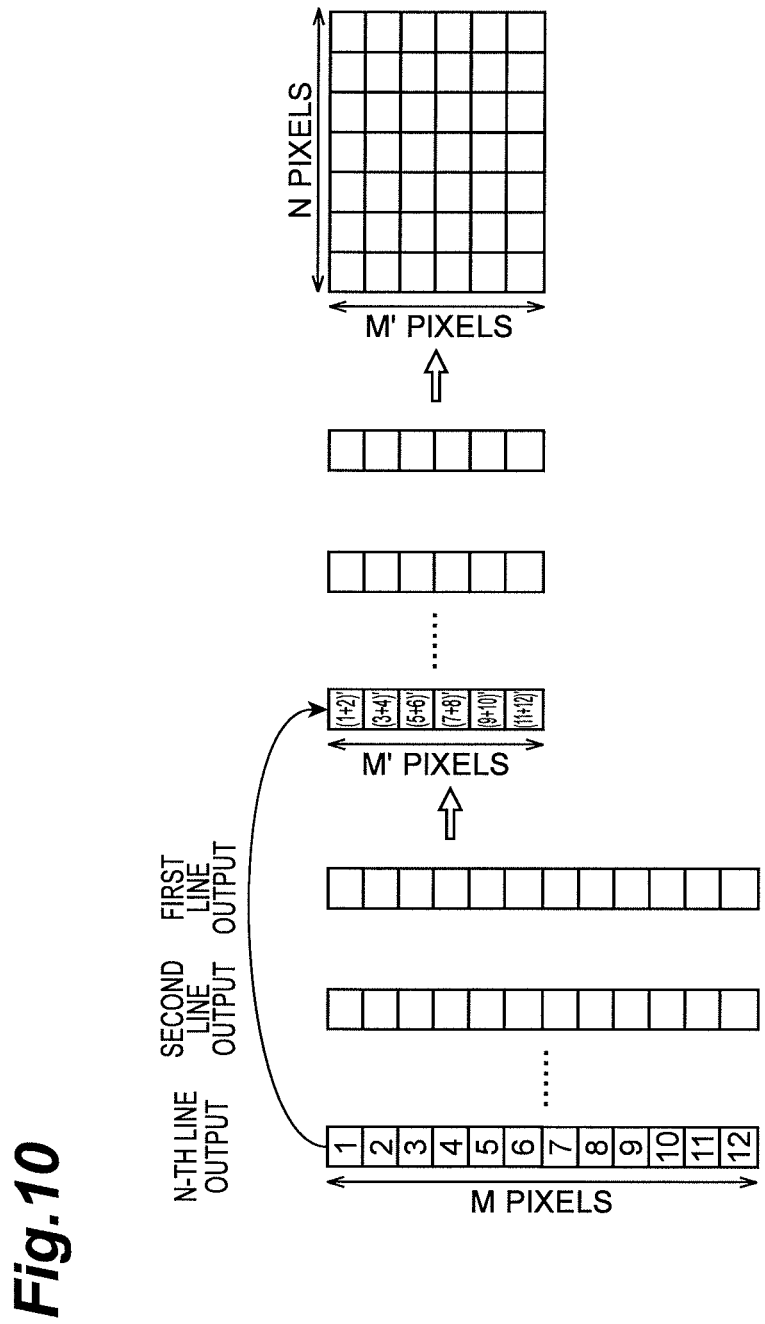
FIG. 10 is a conceptual diagram showing an example of averaging thinning-out processing.

FIG. 10 is a conceptual diagram showing an example of averaging thinning-out processing. In this averaging thinning-out processing, by the pixel change circuit 34d, average brightnesses of pixels adjacent to each other in the image output from the low energy detector 32 are calculated, and pixels with the average brightnesses are arrayed. For example, in FIG. 10, pixels with average brightnesses of {[brightness of first pixel]+[brightness of second pixel]}/2, {[brightness of third pixel]+[brightness of fourth pixel]}/2, { [brightness of fifth pixel]+[brightness of sixth pixel]}/2, {[brightness of seventh pixel]+[brightness of eighth pixel]}/2, { [brightness of ninth pixel]+[brightness of tenth pixel]}/2, and {[brightness of eleventh pixel]+[brightness of twelfth pixel]}/2 are arrayed. In this case, the pixel change circuit 44d outputs the image output from the high energy detector 42 as it is without applying this averaging thinning-out processing thereto.

(2-3) Summing Thinning-Out Processing

Figure 11:
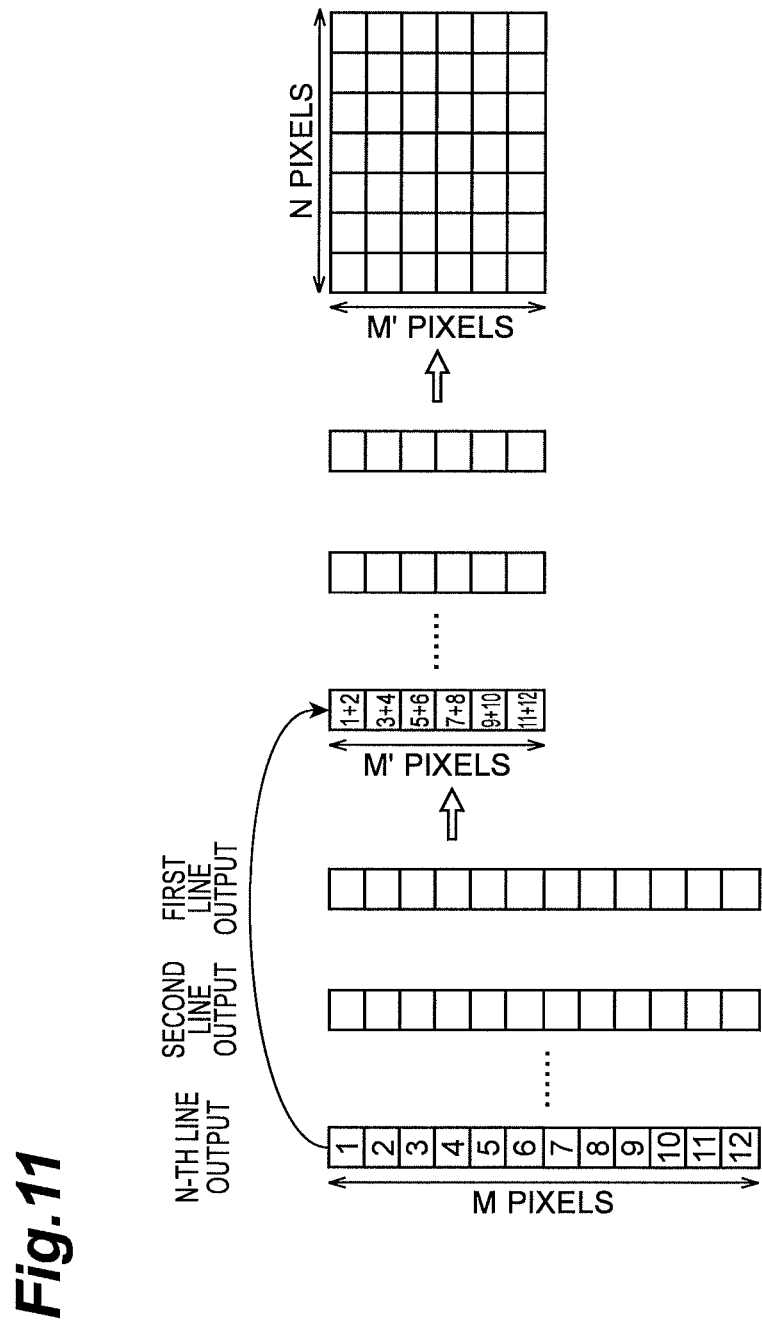
FIG. 11 is a conceptual diagram showing an example of summing thinning-out processing.

FIG. 11 is a conceptual diagram showing an example of summing thinning-out processing. In this summing thinning-out processing, by the pixel change circuit 34d, brightnesses of pixels adjacent to each other in the image output from the low energy detector 32 are summed, and pixels with the sum values are arrayed. For example, in FIG. 11, pixels with sum values of {[brightness of first pixel]+[brightness of second pixel]}, {[brightness of third pixel]+[brightness of fourth pixel]}, {[brightness of fifth pixel]+[brightness of sixth pixel]}, {[brightness of seventh pixel]+[brightness of eighth pixel]}, {[brightness of ninth pixel]+[brightness of tenth pixel]}, and {[brightness of eleventh pixel]+[brightness of twelfth pixel]} are arrayed. In this case, the pixel change circuit 44d outputs the image output from the high energy detector 42 as it is without applying this summing thinning-out processing thereto.

(2-4) Minimum Filter Thinning-Out Processing

Figure 12:
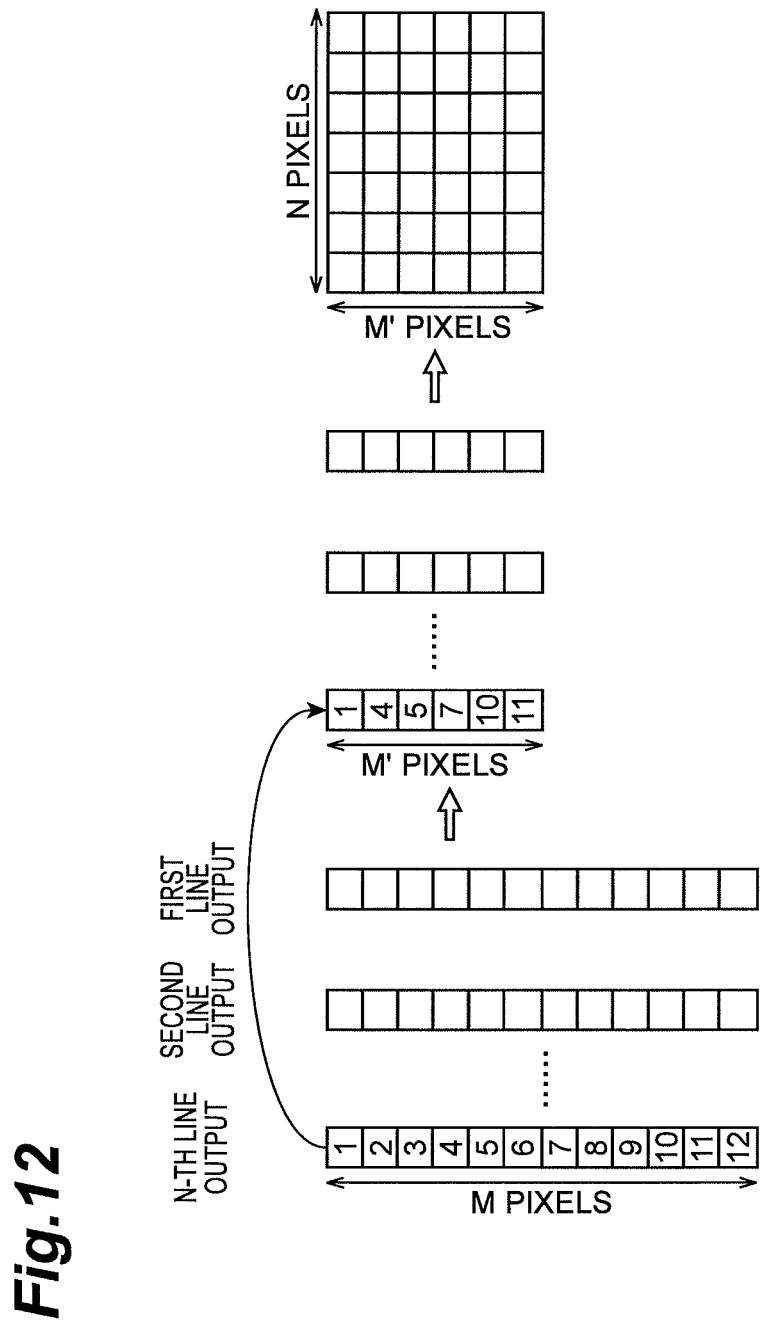
FIG. 12 is a conceptual diagram showing an example of minimum filter thinning-out processing.

FIG. 12 is a conceptual diagram showing an example of minimum filter thinning-out processing. In this minimum filter thinning-out processing, by the pixel change circuit 34d, thinning-out is carried out so that a pixel with the lower brightness of pixels adjacent to each other in the image output from the low energy detector 32 is left and a pixel with the higher brightness is removed. In FIG. 12, on the assumption that [brightness of first pixel]<[brightness of second pixel], [brightness of fourth pixel]<[brightness of third pixel], [brightness of fifth pixel]<[brightness of sixth pixel], [brightness of seventh pixel]<[brightness of eighth pixel], [brightness of tenth pixel]<[brightness of ninth pixel], and [brightness of eleventh pixel]<[brightness of twelfth pixel], and pixels with the higher brightnesses are thinned-out. In this case, the pixel change circuit 44d outputs the image output from the high energy detector 42 as it is without applying this minimum filter thinning-out processing thereto.

In FIG. 12, [number of pixels M]/[number of pixels M']=2, so that brightnesses of pixels adjacent to each other are compared, however, in the case of [number of pixels M]/[number of pixels M']=A, A neighboring pixels are compared, and a pixel with the smallest brightness is left. When the value of A is not an integer, the value may be rounded off.

A foreign substance to be detected in a foreign substance inspection normally has X-ray transmittancy (X-ray absorption) higher than that of the surroundings, so that, as described above, by leaving a pixel with the smaller brightness of pixels adjacent to each other, foreign substance information can be left.

Here, the pixel thinning-out processing can also be generalized as in the case of the above-described primary interpolation processing. For example, when the ratio of the number of pixels of the image from the low energy detector 32 to the number of pixels of the image from the high energy detector 42 is 2 to 1, the pixel change circuit 34d carries out thinning-out processing based on this ratio so as to halve the number of pixels of the image from the low energy detector 32. That is, thinning-out is carried out so that two pixels is reduced to one pixel. Next, when the ratio of the number of pixels of the image from the low energy detector 32 to the number of pixels of the image from the high energy detector 42 is 3 to 1, the pixel change circuit 34d carries out thinning-out processing based on this ratio so as to reduce the number of pixels of the image from the low energy detector 32 to 1/3. Specifically, thinning-out is carried out so that three pixels are reduced to one pixel. Next, when the ratio of the number of pixels of the image from the low energy detector 32 to the number of pixels of the image from the high energy detector 42 is 4 to 3, the pixel change circuit 34d carries out thinning-out so as to reduce the number of pixels of the image from the low energy detector 32 to 1/4. In addition, the pixel change circuit 44d carries out thinning-out so as to reduce the number of pixels of the image from the high energy detector 42 to 1/3.

Accordingly, generalizing the pixel thinning-out processing, when the ratio of the number of pixels of the image from the low energy detector 32 to the number of pixels of the image from the high energy detector 42 is J to K, the pixel change circuit 34d carries out pixel thinning-out so as to reduce the number of pixels of the image from the low energy detector 32 to 1/J, and carries out pixel thinning-out to reduce the number of pixels of the image from the high energy detector 42 to 1/K.

Then, a brightness value of a correction pixel is calculated as follows. When L(x) and L(x+1) are signals of pixels to be corrected, and the pixels of L(x) and L(x+1) are corrected, a brightness value IL(y) of a correction pixel is expressed by the following equation:

$$IL(y)=\gamma(\alpha \times L(x)+\beta \times L(x+1))$$

Here, α is a leading pixel correction factor, β is a following pixel correction factor, γ is a brightness adjustment factor, and x indicates the order of pixels to be corrected. α and β may be arbitrary numbers, or may be calculated. Alternatively, constants may also be used.

According to this generalization, for example, when α=1, β is 0, and γ=1, the above-described simple thinning-out processing is carried out. When α=0.5, β is 0.5, and γ=0.5, the above-described averaging thinning-out processing is carried out. Thus, by calculating α, β, and γ according to the ratio of the numbers of pixels to be used for correction, that is, the numbers of pixels to be used for correction, averaging thinning-out processing and summing thinning-out processing, etc., are realized.

The pixel thinning-out processing is not limited to the above-described simple thinning-out processing, averaging thinning-out processing, summing thinning-out processing, and minimum filter thinning-out processing, but various methods are applicable. For example, various methods may be used such as a thinning-out method using a maximum filter method. The maximum filter method is reverse to the minimum filter method, and a pixel with the larger brightness of pixels adjacent to each other is left. A brightness value of a pixel that passed through a gap becomes higher than brightness values of peripheral pixels. Therefore, by using the maximum filter method, it can be investigated whether a gap is included in a specimen.

Thus, with the radiation detection device 80 according to the present embodiment, even when the pixel width Wa1 in the image detection direction X of the pixel 326 in the low energy detector 32 is smaller than the pixel width Wa2 in the image detection direction X of the pixel 426 in the high energy detector 42, that is, even when the number of pixels per unit length in the low energy detector 32 and the number of pixels per unit length in the high energy detector 42 are different from each other, by the pixel change circuit 34d in the low energy image correction section 34 and the pixel change circuit 44d in the high energy image correction section 44, pixel change processing is carried out so that pixels of an image from the low energy detector 32 and pixels of an image from the high energy detector 42 correspond to each other, and the number of pixels of the image from the low energy detector 32 and the number of pixels of the image from the high energy detector 42 become equal to each other, and therefore, subtraction processing can be easily carried out by the image processing device 70 based on the radiation image acquired with the low energy detector 32 and the radiation image acquired with the high energy detector.

Figure 13:
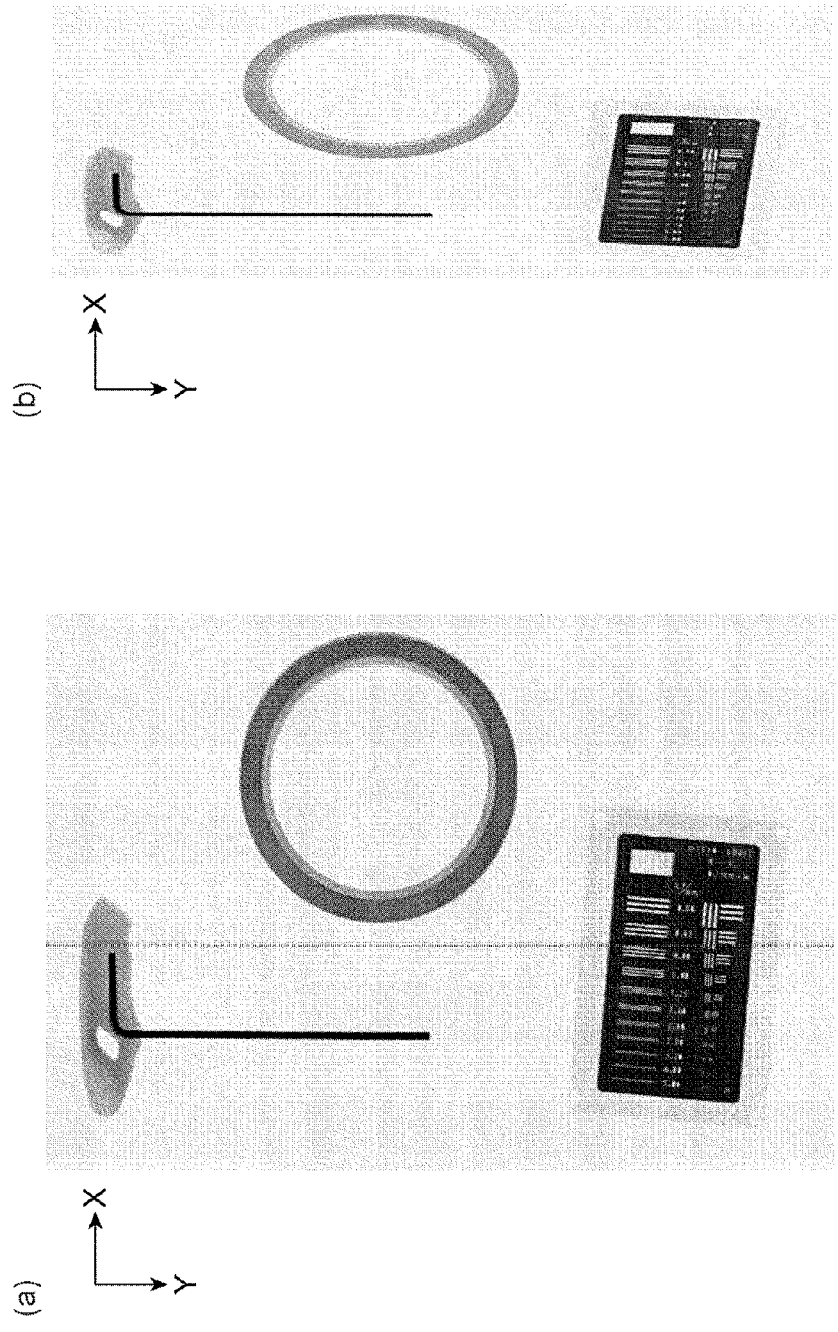
FIG. 13 is a view showing images detected by the low energy detector and the high energy detector when the pixel interpolation processing and the pixel thinning-out processing according to the present embodiment are not applied.
Figure 14:
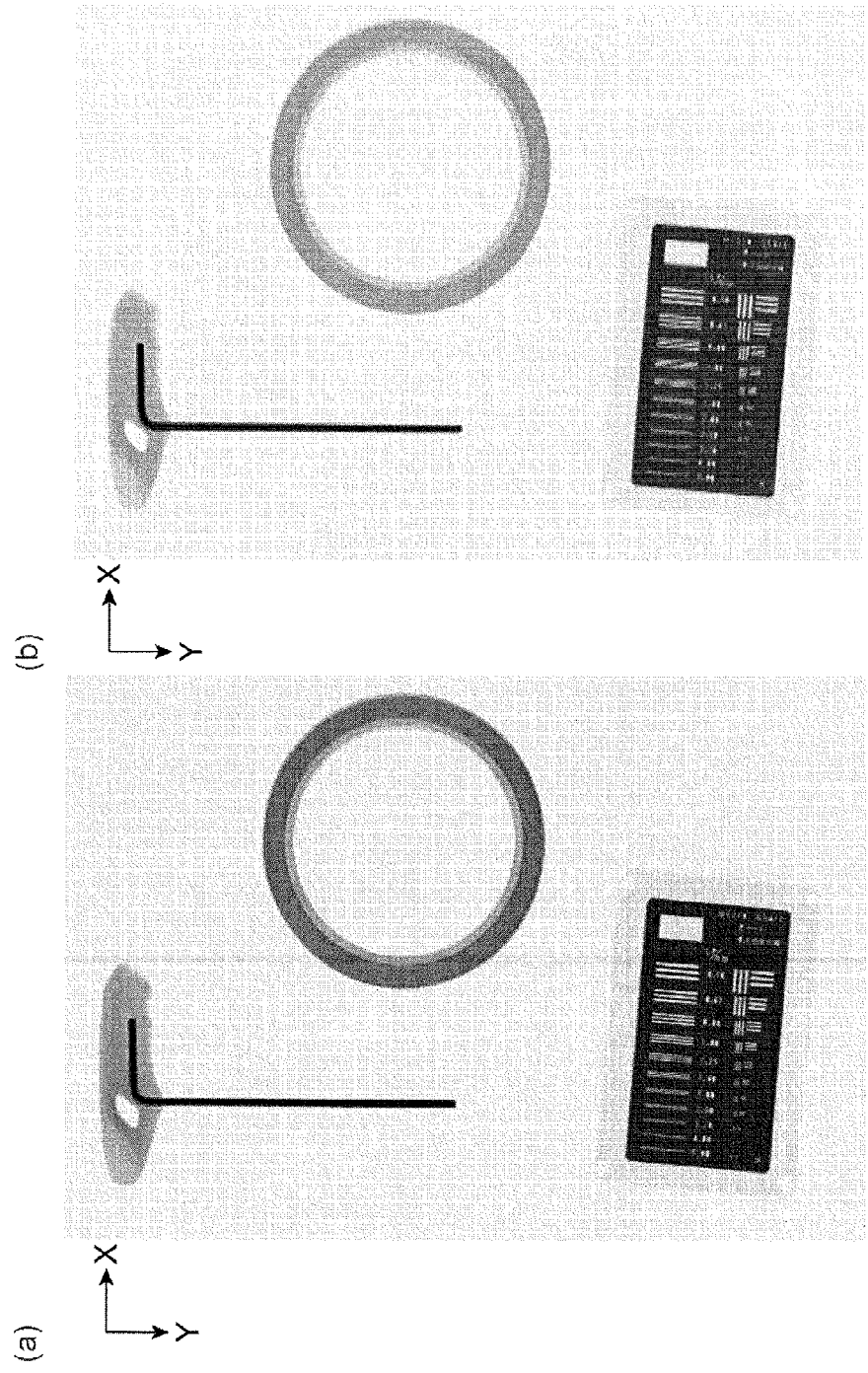
FIG. 14 is a view showing images detected by the low energy detector and the high energy detector when pixel interpolation processing according to the present embodiment is applied.
Figure 15:
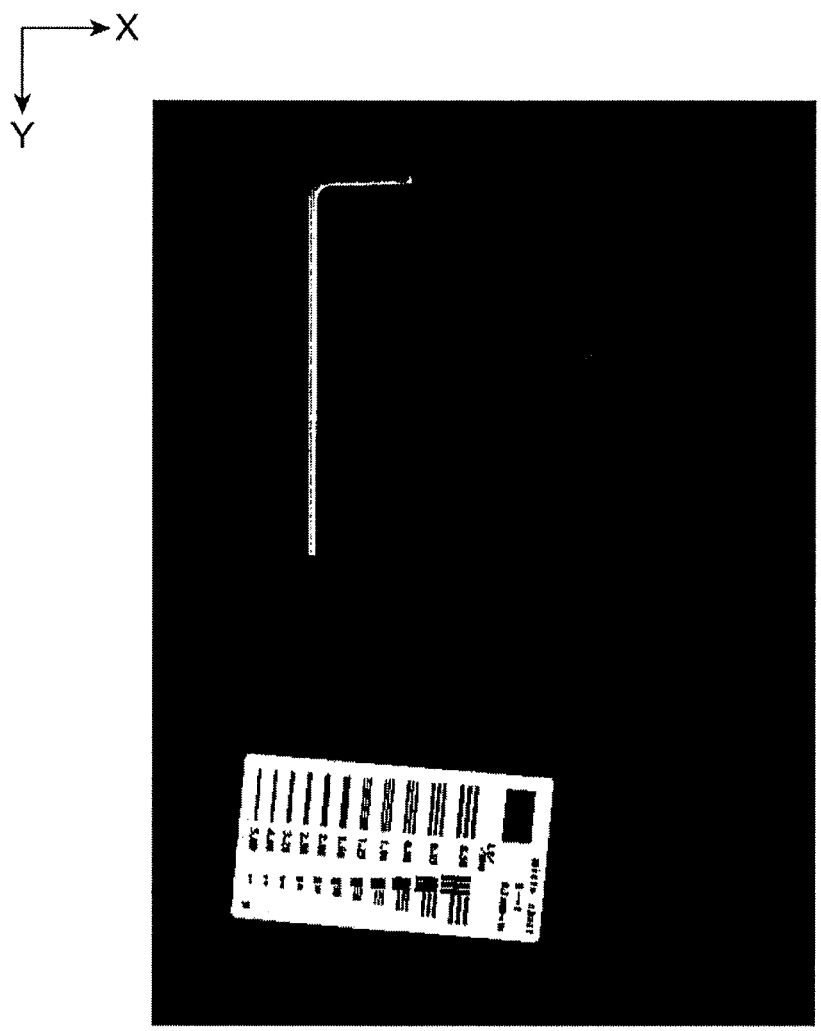
FIG. 15 is a subtraction image based on the images shown in FIG. 14.

FIG. 13 is a view showing an image (a) detected by the low energy detector 32 and an image (b) detected by the high energy detector 42 when the pixel interpolation processing and pixel thinning-out processing of the present embodiment are not applied, and FIG. 14 is a view showing an image (a) detected by the low energy detector 32 and an image (b) detected by the high energy detector 42 when the pixel interpolation processing according to the present embodiment is applied. FIG. 15 shows a subtraction image based on the images shown in FIG. 14.

As shown in FIG. 13, the number of pixels in the detection direction X of the image from the low energy detector 32 and the number of pixels in the detection direction X of the image from the high energy detector 42 are different from each other, so that it is difficult to generate a subtraction image based on these images.

As shown in FIG. 14, by making the number of pixels in the detection direction X of the image from the low energy detector 32 and the number of pixels in the detection direction X of the image from the high energy detector 42 equal to each other, a subtraction image in which only a desired substance is made to stand out can be easily obtained as shown in FIG. 15.

The present invention is not limited to the present embodiment described above, but various modifications are possible.

In the present embodiment, an example in which the low energy image correction section 34 and the high energy image correction section 44 consist of hardware is shown, however, the low energy image correction section 34 and the high energy image correction section 44 may be realized by, for example, software processing in an external computer. Specifically, it is also possible that the image processing section of the present invention is realized by a computer program, and pixel change processing such as pixel interpolation processing and pixel thinning-out processing of the present invention are applied by means of software.

In the present embodiment, to make the areas S1 of the plurality of pixels 326 in the line sensor 324 of the low energy detector 32 smaller than the areas S2 of the plurality of pixels 426 in the line sensor 424 of the high energy detector 42, the pixel width Wa1 of each pixel 326 is made smaller than the pixel width Wa1 of each pixel 426, however, it is also possible that, as shown in FIG. 16, the pixel width Wb1 of each pixel 326 is made smaller than the pixel width Wb2 of each pixel 426. Thus, when the numbers of line outputs in the conveying direction Y are different from each other, the detection timings of the two radiation detectors may be adjusted so that the numbers of line outputs become equal to each other.

Industrial Applicability

The present invention is applicable to uses that make easy arithmetic processing based on radiation images acquired with two radiation detectors even when the numbers of pixels of the radiation detectors are different from each other.

REFERENCE SIGNS LIST

1 X-ray foreign substance inspection device
10 Belt conveyor
12 Belt portion
14 Belt conveyor control section
20 X-ray irradiator
30 Low energy image acquisition section
32 Low energy detector (first radiation detector)
322 Low energy scintillator layer (first scintillator layer)
324 Low energy line sensor (first pixel section)
326 Pixel
34 Low energy image correction section (first image processing section)
34a Amplifier
34b A/D converter 34c Correction circuit
34d Pixel change circuit
34e Output interface
40 High energy image acquisition section
42 High energy detector (second radiation detector)
422 High energy scintillator layer (second scintillator layer)
424 High energy line sensor (second pixel section)
426 Pixel
44 High energy image correction section (second image processing section)
44a Amplifier
44b A/D converter
44c Correction circuit
44d Pixel change circuit
44e Output interface
50 Timing control section
70 Image processing device
80 Radiation detection device
86 Dual-energy sensor

The invention claimed is:

1. A radiation detection device for a foreign substance inspection using a subtraction method, which detects radiation in a first energy range and radiation in a second energy range higher than the radiation in the first energy range that are transmitted through a specimen and incident from a radiation incident direction, comprising:
a first radiation detector that is positioned on the upstream side with respect to the radiation incident direction, and detects radiation in the first energy range and generates a first image corresponding to an image of the radiation;
a second radiation detector that is positioned on the downstream side with respect to the radiation incident direction, and detects radiation in the second energy range and generates a second image corresponding to an image of the radiation;
a first image processing section that applies image processing to the first image from the first radiation detector; and
a second image processing section that applies image processing to the second image from the second radiation detector, wherein
the first radiation detector includes a first pixel section that has a plurality of pixels arrayed along an image detection direction and acquires the first image based on the image of the radiation in the first energy range,
the second radiation detector includes a second pixel section that has a plurality of pixels arrayed along the image detection direction and acquires the second image based on the image of the radiation in the second energy range,
a first pixel width in the image detection direction of each of the plurality of pixels in the first pixel section is smaller than a second pixel width in the image detection direction of each of the plurality of pixels in the second pixel section, and
the first image processing section and the second image processing section carry out pixel change processing to make the number of pixels of the first image and the number of pixels of the second image equal to each other.

2. The radiation detection device according to claim 1, wherein
the first image processing section and second image processing section applies pixel thinning-out processing to at least one of the number of pixels of the first image and the number of pixels of the second image.

3. The radiation detection device according to claim 2, wherein
the thinning-out processing is simple thinning-out processing, averaging thinning-out processing, summing thinning-out processing, minimum filter thinning-out processing, or maximum filter thinning-out processing.

4. The radiation detection device according to claim 2, wherein
in the thinning-out processing,
based on a ratio J to K of the number of pixels of the first image to the number of pixels of the second image, one correction pixel is generated from two pixels adjacent to each other of at least one of the pixels of the first image and the pixels of the second image so that the number of pixels of the first image becomes 1/J times and the number of pixels of the second image becomes 1/K times, and
a brightness value IL(y) of the correction pixel is set to satisfy the following equation:

$$IL(y)=\gamma(\alpha \times L(x)+\beta \times L(x+1))$$

based on signal values L(x) and L(x+1) of the two pixels before being corrected, pixel correction factors α and β, and a brightness adjustment factor γ.

5. The radiation detection device according to claim 1, wherein t
the first image processing section and second image processing section apply pixel interpolation processing to at least one of the number of pixels of the first image and the number of pixels of the second image.

6. The radiation detection device according to claim 5, wherein
the interpolation processing is simple interpolation processing, primary interpolation processing, secondary interpolation processing, spline interpolation processing, or Lagrange interpolation processing.

7. The radiation detection device according to claim 5, wherein
in the interpolation processing,
based on the ratio J to K of the number of pixels of the first image to the number of pixels of the second image and a least common multiple L of J and K, interpolation pixels are interpolated for at least one of among the pixels of the first image and among the pixels of the second image so that the number of pixels of the first image becomes L/J times and the number of pixels of the second image becomes L/K times, and
a brightness value IH(y) of the interpolation pixel is set to satisfy the following equation:

$$IH(y)=\gamma(\alpha \times H(x)+\beta \times H(x+1))$$

based on signal values H(x) and H(x+1) of the pixels adjacent on both sides to the interpolation pixel, pixel correction factors α and β, and a brightness adjustment factor γ.

8. The radiation detection device according to claim 1, wherein
the first radiation detector includes a first scintillator layer that extends along the image detection direction and converts an image of radiation in the first energy range into an optical image, and a first pixel section that acquires the first image based on the optical image converted by the first scintillator layer, and
the second radiation detector includes a second scintillator layer that extends along the image detection direction and converts an image of radiation in the second energy range into an optical image, and a second pixel section that acquires the second image based on the optical image converted by the second scintillator layer.

9. A system for acquiring a radiation image of an object, comprising:
- a conveyor configured to convey the object in a conveying direction;
- a first radiation detector arrayed a plurality of pixels along an image detection direction which intersects with the conveying direction and configured to detect radiation which are transmitted through the object and output first image data;
- a second radiation detector arrayed a plurality of pixels along the image detection direction and configured to detect radiation which are transmitted through the first radiation detector and output second image data; and
- an image processing device configured to generate a subtraction image on the basis of the first image data and the second image data; wherein
- a first pixel width of each of the plurality of pixels in the first detector is smaller than a second pixel width of each of the plurality of pixels in the second pixel section, and
- the image processing device carries out pixel change processing to make the number of pixels of the first image data and the number of pixels of the second image data equal to each other.

10. The system for acquiring a radiation image of an object according to claim 9, wherein
- the first radiation detector includes a first scintillator layer that extends along the image detection direction and is configured to convert an image of radiation in the first energy range into an optical image, and a first pixel section that is configured to acquire the first image based on the optical image converted by the first scintillator layer, and
- the second radiation detector includes a second scintillator layer that extends along the image detection direction and is configured to convert an image of radiation in the second energy range into an optical image, and a second pixel section that is configured to acquire the second image based on the optical image converted by the second scintillator layer.

11. The system for acquiring a radiation image of an object according to claim 9, wherein:
the pixel width is the width in an image detection direction.

12. The system for acquiring a radiation image of an object according to claim 9, wherein:
the pixel width is the width in a direction orthogonal to the image detection direction.

13. A method of acquiring a radiation image of an object, comprising:
- conveying the object in a conveying direction;
- by a first radiation detector arrayed a plurality of pixels along an image detection direction which intersects with the conveying direction, detecting radiation which are transmitted through the object and outputting first image data;
- by a second radiation detector arrayed a plurality of pixels along the image detection direction, detecting radiation which are transmitted through the first radiation detector and outputting second image data;
- processing so as to make the number of pixels of the first image data and the number of pixels of the second image data equal to each other; and
- generating a subtraction image on the basis the processed image data; wherein
- a first pixel width of each of the plurality of pixels in the first detector is smaller than a second pixel width of each of the plurality of pixels in the second pixel section.

14. The method of acquiring a radiation image of an object, according to claim 13, wherein
- the first radiation detector includes a first scintillator layer that extends along the image detection direction and converts an image of radiation in the first energy range into an optical image, and a first pixel section that acquires the first image based on the optical image converted by the first scintillator layer, and
- the second radiation detector includes a second scintillator layer that extends along the image detection direction and converts an image of radiation in the second energy range into an optical image, and a second pixel section that acquires the second image based on the optical image converted by the second scintillator layer.

15. The method of acquiring a radiation image of an object according to claim 13, wherein:
the pixel width is the width in an image detection direction.

16. The method of acquiring a radiation image of an object according to claim 13, wherein:
the pixel width is the width in a direction orthogonal to the image detection direction.

* * * * *